United States Patent [19]

Srivastava et al.

[11] Patent Number: 5,571,796
[45] Date of Patent: Nov. 5, 1996

[54] ADMINISTRATION OF VALIENAMINE-RELATED DISACCHARIDE COMPOUNDS IN REDUCING INFLAMMATION IN A SENSITIZED MAMMAL ARISING FROM EXPOSURE TO AN ANTIGEN

[75] Inventors: Om P. Srivastava; Roman Szweda; Richard H. Smith, all of Edmonton; Robert M. Ippolito, West Edmonton, all of Canada; Ulrike Spohr, Boulder, Colo.

[73] Assignee: Alberta Research Council, Edmonton, Canada

[21] Appl. No.: 466,621

[22] Filed: Jun. 6, 1995

[51] Int. Cl.[6] .............................. A61K 31/70; C07H 5/04
[52] U.S. Cl. .............................. 514/42; 514/53; 536/17.9; 536/18.7; 564/462
[58] Field of Search .................................. 514/23, 62, 42, 514/53; 536/18.7, 17.9; 564/462

[56] References Cited

U.S. PATENT DOCUMENTS

4,595,678  6/1986  Horii et al. .............................. 514/53

FOREIGN PATENT DOCUMENTS

0049981  4/1982  European Pat. Off. .
0089812  9/1983  European Pat. Off. .
57-54593  4/1982  Japan .
8605094  9/1986  WIPO .

OTHER PUBLICATIONS

Ogawa et al.(I), "Synthesis of Adiposin–1, α–Glycoside Hydrolase Inhibitor," *Chemistry Letters*, (3), 337–340 (1983).
Asano et al.(I), "Microbial Degradation of Validamycin A by *Flavobacterium Saccharophilum*," *J. Antibiotics*, 37(8), 859–867 (1984).
Ogawa et al., (II), "Total Synthesis of (+)–Validamycin," *J. Chem. Soc., Chem. Comm.*, (24), 1843–1844 (1987).
Yoshikawa et al., "Synthesis of Validamine, *epi*–Validamine, and Valienamine, Three Optically Active *pseudo*–Amino–Sugars, From D–Glucose," *Chem. Pharm. Bull.*, 36 (10), 4236–4239 (1988).
Kameda et al.(I), "New Cyclitols, Degradation of Validamycin A by *Flavobacterium Saccharophilum*," *J. Antibiotics*, 33 (12), 1573–1574 (1980).
Kameda et al.(II), "Valienamine as an α–Glycosidase Inhibitor," *J. Antibiotics*, 33(12), 1575–1576 (1980).
Furumoto et al., "Enzymatic Synthesis of Valienamine Glycosides and Their Antibiotic Activity," *J. Antibiotics*, 44 (3), 371–373 (1991).
Asano et al.(II), "All Eight Possible Mono–β–D–Glycosides of Validoxylamine A–I. Preparation and Structure Determination," *J. Antibiotics*, 44 (12), 1406–1416 (1991).
Asano et al.(III), "All Eight Possible Mono–β–D–Glycosides of Validoxylamine A–II. Biological Activities," *J. Antibiotics*, 44 (12), 1417–1421 (1991).

Ogawa et al.(III), "Synthesis of Potent α–Glycosidase Inhibitors: Methyl Acarviosin Analogue Composed of 1,6–Anhydro–β–D–glucopuranose Residue," *J. Chem. Soc., Chem. Comm.*, (20), 1387–1388 (1990).
Ogawa et al.(IV), "Synthesis and Enzyme–Inhibitory Activity of Methyl Acarviosin Analogues Having the α–*manno* Configuration," *Carbohydrate Research*, 226, 79–89 (1992).
Ogawa et al.(V), "Chemical Modification of the Sugar Moiety of Methyl Acarviosin: Synthesis and Inhibitory Activity of Eight Analogues Containing a 1,6–Anhydro Bridge," *Carbohydrate Research*, 250, 177–184 (1993).
Smith and Ziola, "Cyclophosphamide and dimethyl dioctadecyl ammonium bromide immunopotentiate the delayed––type hypersensitivity response to inactivated enveloped viruses", *Immunology* 58: 245–250 (1986).
Ogawa et al., "Synthetic Studies on Antibiotic Validamycins, Part 12. [1,2]Total Synthesis of (+)–Validamycin B and (+)–Validoxylamine B", *J. Chem. Soc. Perkin Trans* 1:2675–2680 (1988).
Cerny et al., "Preparation of 2–Amino–1, 6–Anhydro–2–Deoxy–β–D–Glucopyranose and 2–Amino–1,6 3,4–Dianhydro–2–Deoxy–β–D–Galactopyranose", *Collection Czechoslav. Chem. Commun.* 39:1391–1396 (1974).
Hayashida et al., "Novel Synthesis Of Penta–N, O–Acetylvaliolamine", *J. Carbohydrate Chemistry*, 7(1):83–94 (1988).
Ray and Matteson, "Osmium Tetroxide Catalyzed Hydroxylation of Hindered Olefins", *Tetrahedron Lett.* 21:499–450 (1980).
Kameda et al., "Valiolamine, a New α–Glucosidase Inhibiting Aminocyclitol Produced by *Streptomyces Hygroscopicus*", *J. Antibio.* 37:1301–1307 (1984).
Takeuchi et al., "Inhibitory Effect of Validamine, Valienamine and Valiolamine on Activities of Carbohydrases in Rat Small Intestinal Brush Border Membranes", *Chem. Pharm. Bull* 38(7):1970–1972 (1990).
Ogawa et al., "Synthetic Studies on the Validamycins 5.[1,2] Synthesis of DL–Hydroxyvalidamine and DL–Valienamine", *J. Org. Chem.* 48:1203–1207 (1983).
Paulsen et al., "Synthese von Pseudozuckern aus D–Glucose durch intramolekulare Horner–Emmons–Olefinierung", *Liebigs Ann Chem.* 125–131 (1987).
Kobayashi and Shiozaki, "Syntheses of Trehazolin Derivatives and Evaluation as Glycosidase Inhibitors", *J. Org. Chem.* 60:(8) 2570–2580 (1995).

*Primary Examiner*—John Kight
*Assistant Examiner*—L. Eric Crane
*Attorney, Agent, or Firm*—Burns, Doane, Swecker & Mathis, L.L.P.

[57] ABSTRACT

The present invention is directed to methods of reducing the degree of inflammation arising from a secondary immune response in a mammal due to antigen exposure (challenge) by the administration of valienamine-related disaccharide compounds and the pharmaceutical compositions employed in the method.

11 Claims, 4 Drawing Sheets

1D-(1,2,413,5)-1-amino-2,3,4-tri-O-benzyl-5-c-benzyloxymethyl-1,2,3,4-cyclohexane tetrol

ADMINISTRATION OF VALIENAMINE-RELATED DISACCHARIDE COMPOUNDS IN REDUCING INFLAMMATION IN A SENSITIZED MAMMAL ARISING FROM EXPOSURE TO AN ANTIGEN

BACKGROUND OF THE INVENTION

1. Field of the Invention

The present invention is directed, in part, to the discovery that valienamine-related disaccharide compounds reduce, in vivo, the degree of inflammation arising from a secondary immune response in a mammal due to antigen exposure (challenge).

Specifically, this invention is directed to methods of reducing the degree of inflammation arising from a secondary immune response in a mammal due to antigen exposure (challenge) by the administration of valienamine-related compounds and to pharmaceutical compositions comprising such valienamine-related compounds.

2. References

The following publications and patent application are cited in this application as superscript numbers at the relevant portion of the application:

1. Ippolito et al., U.S. patent application Ser. No. 08/081,214 for "TIME DEPENDENT ADMINISTRATION OF OLIGOSACCHARIDE GLYCOSIDES RELATED TO BLOOD GROUP DETERMINANTS HAVING A TYPE I OR TYPE II CORE STRUCTURE IN REDUCING INFLAMMATION IN A SENSITIZED MAMMAL ARISING FROM EXPOSURE TO AN ANTIGEN" filed Jun. 25, 1993
2. Smith and Ziola, *Immunology* 58:245 (1986)
3. Ogawa et al., *J. Chem. Soc. Perkin Trans* 1:2675–2680 (1988)
4. Cerny et al., *Collection Czechoslav. Chem. Commun.* 39:1391–1396 (1974)
5. Hayashida et al., *J. Carbohydrate Chemistry* 7(1):83–94 (1988)
6. Ray and Matteson, *Tetrahedron Lett.* 21:449 (1980)
7. Kameda et al., *J. Antibio.* 37:1301–1307 (1984)
8. Takeuchi et al., *Chem. Pharm. Bull* 38(7):1970–1972 (1990)
9. Ogawa et al., *J. Org. Chem.* 48:1203–1207 (1983)
10. Paulson et al., *Liebigs Ann Chem.* 125–131 (1987)

All of the above publications and patent applications are herein incorporated by reference in their entirety to the same extent as if each individual publication or patent application was specifically and individually indicated to be incorporated by reference in its entirety.

3. State of the Art

The administration to mammals of different oligosaccharide glycosides has been disclosed in the art to reduce inflammation in the mammal arising from a variety of conditions such as injury, infection, exposure to an antigen, etc. These disclosures are based on the fact that an integral step in the inflammatory process in a mammal is the adherence of leukocytes to one or more selectins and the discovery that such oligosaccharide glycosides adhere/bind to one or more selectins involved in the inflammatory response thereby interfering with the binding of the leukocyte to those selectins.

Allowed U.S. patent application Ser. No. 08/081,214[1] discloses that in order to reduce inflammation in the case of an antigen challenge (exposure) in a sensitized mammal, the oligosaccharide glycoside must be administered after initiation of the mammal's secondary immune response to the antigen challenge but at or prior to one-half the period of time where the mammal experiences maximal inflammatory response.

However, it was found that after administration of oligosaccharide glycosides to a mammal, the oligosaccharides were quickly cleared from the mammalian system. Accordingly, it was desired to identify pseudo-oligosaccharides which would not be cleared from the mammalian system as quickly as oligosaccharide glycosides and still retain activity in reducing the degree of inflammation in a mammal arising from initiation of a mammal's secondary immune response due to antigen exposure. In other words, compounds were desired that were more resistant to degradation in the mammalian body and able to withstand denaturation in the stomach and/or removal from the blood stream by action of glycosidases.

It is known in the art that the pseudo-aminosugars, validamine, valienamine and valiolamine, show inhibition of α-glucosidases, sucrase and maltase in vitro and of sucrase, maltase, glucoamylase, isomaltase and trehalase in vivo. (Takeuchi et al., (1990)[8] Ogawa et al., *J. Org. Chem.* 48:1203–1207 (1983))[9] also describe the compound valienamine-α-1,4-glucose. However, it was not known if such pseudo-aminosugars or pseudo-disaccharides containing such sugars would be effective in reducing the degree of inflammation arising from a secondary immune response in a mammal due to antigen exposure.

As shown herein valienamine-related disaccharide compounds are able to reduce the degree of inflammation arising from a secondary immune response. Further advantages of the present invention will become apparent from the following description of the invention with reference to the attached drawings.

SUMMARY OF THE INVENTION

In one of its method aspects, this invention is directed to a method for reducing the degree of inflammation in a mammal arising from the initiation of a mammal's secondary immune response due to antigen exposure, which method comprises administering to said mammal an inflammation reducing effective amount of an valienamine-related disaccharide compound and pharmaceutically acceptable salts thereof.

In another of its method aspects, this invention is directed to a method for reducing the degree of inflammation in a mammal arising from the initiation of a mammal's secondary immune response due to antigen exposure, which method comprises administering to said mammal a valienamine-related disaccharide compound selected from the group consisting of Formula I

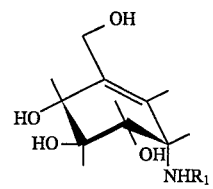

and Formula II

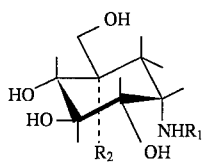

where $R_1$ is selected from the group consisting of glucose and 1,6-anhydroglucose;

where $R_2$ is selected from the group consisting of —H and —OH; and pharmaceutically acceptable salts thereof.

In one of its composition aspects, this invention is directed to α-5,2-valiolamine disaccharides comprising

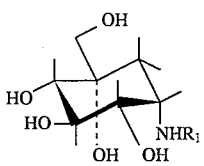

where $R_1$ is selected from the group consisting of glucose and 1,6-anhydroglucose; and pharmaceutically acceptable salts thereof.

In another of its composition aspects, this invention is directed to α-1,2-valienamine-related disaccharides selected from the group consisting of Formula I

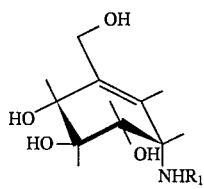

and Formula II

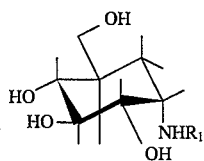

where $R_1$ is selected from the group consisting of glucose and 1,6-anhydroglucose; and pharmaceutically acceptable salts thereof.

In another of its composition aspects, this invention is directed to pharmaceutical compositions comprising a pharmaceutically inert carrier and an α-5,2-valiolamine disaccharide comprising

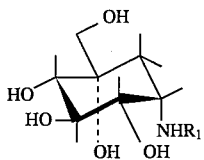

where $R_1$ is selected from the group consisting of glucose and 1,6-anhydroglucose; and pharmaceutically acceptable salts thereof.

In another of its composition aspects, this invention is directed to pharmaceutical compositions comprising a pharmaceutically inert carrier and an α-1,2-valienamine-related disaccharide selected from the group consisting of

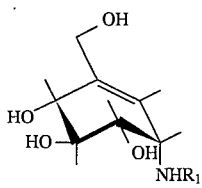

and Formula II

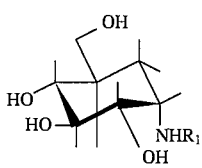

where $R_1$ is selected from the group consisting of glucose and 1,6-anhydroglucose; and pharmaceutically acceptable salts thereof.

Preferable, in such pharmaceutical compositions, the valienamine-related disaccharide compounds comprise from 1 to about 95 weight percent of the total weight of the pharmaceutical composition.

DETAILED DESCRIPTION OF THE PREFERRED EMBODIMENTS

Figure 1:
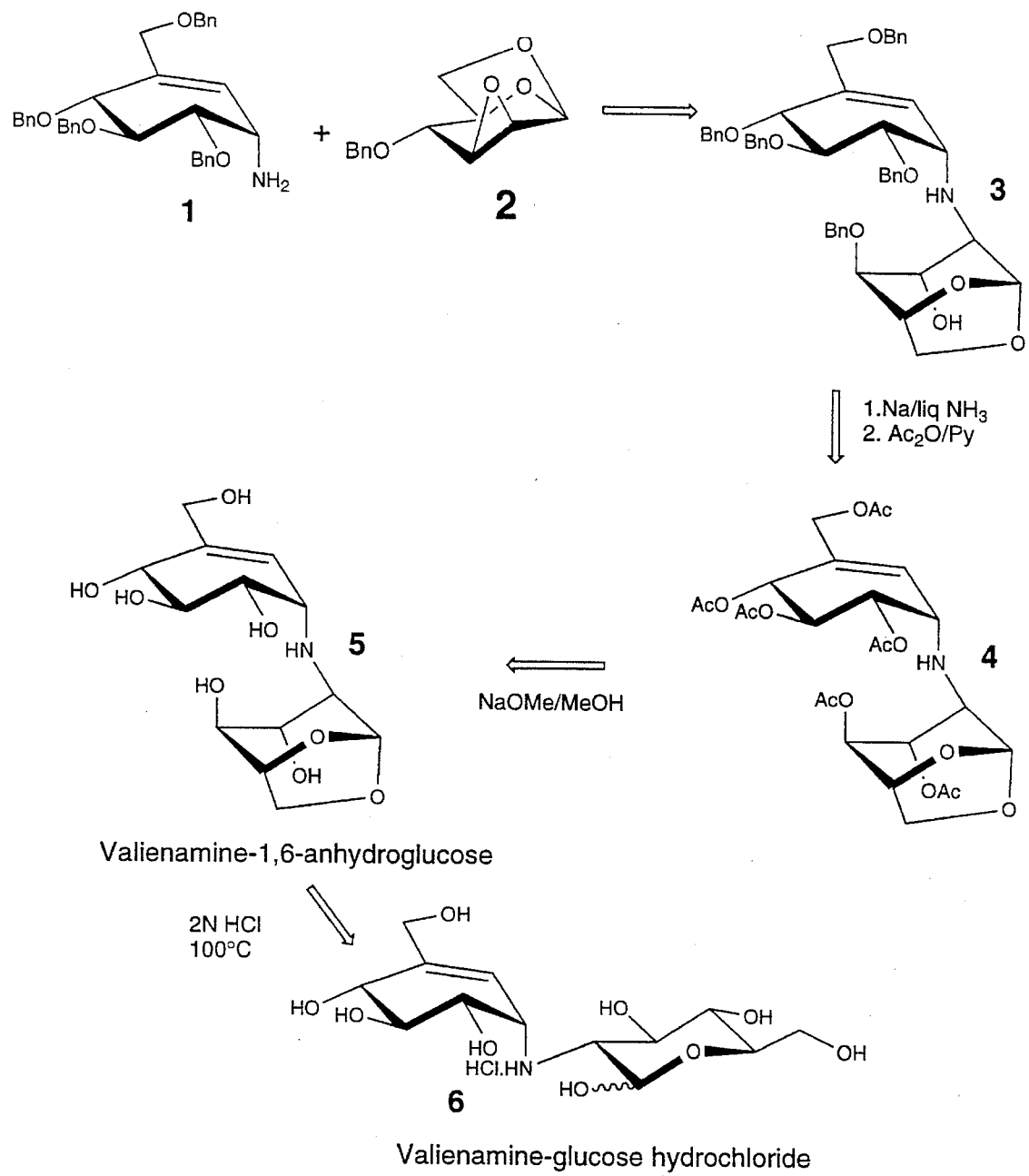
FIG. 1 illustrates the synthesis of valienamine-1,6-anhydroglucose and valienamine-glucose.

As noted above this invention is directed to the discovery that a reduction in antigen induced inflammation in sensitized mammals can be achieved by the administration of valienamine-related disaccharide compounds.

However, prior to discussing this invention in further detail, the following terms will first be defined.

1. Definitions

As used herein the following terms have the definitions given below:

The term "sensitized mammal" refers to those mammals which have been previously exposed to an antigen and, accordingly, their immune systems have become educated to that antigen. Typically, initial exposure of an antigen to a mammal primes or educates the mammal's immune response to later exposure to that antigen with minimal inflammation during such initial exposure.

The term "secondary immune response" refers to the effector phase of a mammal's immune response to an antigen to which it has been previously been sensitized. A mammal's secondary immune response is typically accompanied by inflammation at the point of antigen exposure.

The term "antigen" refers to any protein, peptide, carbohydrate, nucleic acid or other non-endogenous substance which when exposed to a mammal induces an immune response in that mammal.

The term "period for maximal inflammation" refers to the period of time typically required to achieve maximal exposure to a specific antigen. This period of time depends on several factors such as the specific antigen to which the mammal has been exposed, the particular mammalian species exposed to the antigen, etc. Accordingly, the period of time required to effect maximal antigen induced inflammation in a sensitized mammal will vary for, by way of example, asthma as opposed to rheumatoid arthritis.

Disease conditions attributable to antigen exposure include, by way of example, psoriasis, asthma, dermatitis, rheumatoid arthritis, delayed type hypersensitivity, inflammatory bowel disease, multiple sclerosis, viral pneumonia, bacterial pneumonia, and the like.

The term "pharmaceutically acceptable salts" includes the pharmaceutically acceptable addition salts of valienamine-related disaccharide compounds capable of forming salts and are derived from a variety of organic and inorganic counter salts well known in the art and include, by way of example only, sodium, potassium, calcium, magnesium, ammonium, tetralkylammonium, chloride, fluoride, bromide, hydroxide and the like.

The term "removable blocking group" or "blocking group" refers to any group which when bound to one or more hydroxyl and/or amine groups of valienamine-related compounds and valienamine-related disaccharide compounds prevents reactions from occurring at these hydroxyl and/or amine groups and which protecting group can be removed by conventional chemical or enzymatic steps to reestablish the hydroxyl or amine group. The particular removable blocking group employed is not critical and preferred removable hydroxyl blocking groups include conventional substituents such as benzyl, acetyl, chloroacetyl, benzylidene, t-butyl-diphenylsilyl and any other group that can be introduced either enzymatically or chemically onto a hydroxyl functionality and later selectively removed either by enzymatic or chemical methods in mild conditions compatible with the nature of the product. Preferred amine blocking groups include these well known in the art such as carboxybenzyloxy (CBZ), t-butyloxy carbonyl (t-Boc), and any other group that can be introduced either enzymatically or chemically onto an amine functionality and later selectively removed either by enzymatic or chemical methods in mild conditions compatible with the nature of the product.

The term "valienamine-related compounds" means all naturally occurring structures related to valienamine and analogues of structures related to valienamine.

Naturally occurring structures related to valienamine include, by way of example, valiolamine and validamine. A complete list of naturally occurring structures related to valienamine known to date are provided by Kameda et al., *J. Antibiol.* 37:1301–1307[7].

Analogues of structures related to valienamine refers to analogues of naturally occurring structures of valienamine, valiolamine and validamine including those wherein the valienamine, valiolamine or validamine has been chemically modified so as to introduce and/or remove one or more functionalities from such structures. For example, modification can result in the removal of an —OH functionality (i.e. the formation of a deoxy substituent), the introduction of an amine functionality, the introduction of a halo functionality, conversion of one or more hydroxyl groups to ester, ether or carbamate functional groups, and the like; provided that such chemical modifications do not destroy the biological activity of the valienamine-related disaccharide analogues.

The term "valienamine-related disaccharide compounds" means all disaccharide compounds containing valienamine-related compounds.

Preferred valienamine-related disaccharide compounds include compounds having Formula I

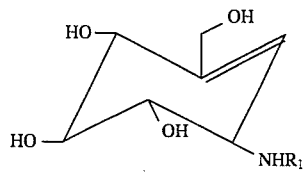

and Formula II

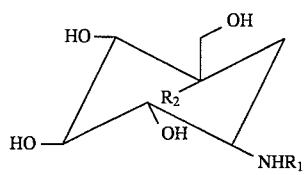

where $R_1$ is selected from the group consisting of glucose and anhydroglucose;

where $R_2$ is selected from the group consisting of —H and —OH; and pharmaceutically acceptable salts thereof. Particularly preferred are compounds of Formula I having an α-1, 2-linkage and those of Formula II where $R_2$ is —OH having an α-5,2-linkage and where $R_2$ is —H having an α-1,2-linkage.

2. Methodology

As shown below in the examples, valienamine-related disaccharide compounds are effective in reducing the degree of antigen induced inflammation in a sensitized mammal.

The valienamine-related disaccharide compounds are preferably administered to a mammalian patient alter initiation of the mammal's secondary immune response to that antigen and more preferably at least about 0.5 hours after exposure to an antigen; still more preferably, from at least about 0.5 to about 10 hours after exposure to the antigen and most preferably from at least about 3 hours to 7 hours after antigen exposure. In a particularly preferred embodiment, the valienamine-related disaccharide compound is administered to the patient after initiation of that patient's secondary immune response to antigen exposure but prior to one-half period of time required for maximal inflammation due to antigen exposure.

The valienamine-related disaccharide compounds are effective in reducing antigen induced inflammation in a sensitized mammal when administered at a dosage range of from about 5 mg to about 20 mg/kg of body weight, and preferably from about 7 mg to about 15 mg/kg of body weight. The specific dose employed is regulated by the particular antigen induced inflammation being treated as well as by the judgement of the attending clinician depending upon factors such as the severity of the inflammation, the age and general condition of the patient, and the like. The pharmaceutical compositions described herein can be administered in a single dose or in multiple doses or in a continuous infusion over the critical time frame.

It is contemplated that these compounds would be useful for the treatment of ischemia reperfusion injury, such as myocardial reperfusion, severing reperfusion injury due to attachment of a severed limb, contact sensitivity, adult respiratory distress syndrome and possibly treatment of cancer metastases. It is further contemplated that the compounds of the present invention will also inhibit glucosidases and thus be useful in the dietary management of carbohydrate-dependent metabolic disorders such as diabetes, obesity, hyperglycemia and hyperlipemia. When so used, the dosage of the compounds would be that set forth above for the reduction of inflammation.

When employed as pharmaceuticals, the valienamine-related disaccharide compounds above are usually administered in the form of pharmaceutical compositions. Pharmaceutical compositions having valienamine-related disaccharide compounds are preferably administered parenterally, intranasally, intrapulmonarily, transdermally and intravenously, although other forms of administration are contemplated. These compounds are effective as both injectable and oral compositions. Such compositions are prepared in a manner well known in the pharmaceutical art and comprise at least one active compound.

The methods of this invention are preferably achieved by use of a pharmaceutical composition suitable for use in the parenteral administration of an effective amount of a valienamine-related disaccharide compound. These compositions comprise a pharmaceutically inert carrier such as water, buffered saline, etc. and an effective amount of a valienamine-related disaccharide compound (or mixtures thereof) so as to provide the above-noted dosage of the valienamine-related compound when administered to a patient. It is contemplated that suitable pharmaceutical compositions can additionally contain optional components such as a preservative, etc.

It is further contemplated that suitable pharmaceutical compositions can include oral compositions, transdermal compositions or bandages etc., which are well known in the art. Therefore, the compositions can be in the form of tablets, pills, powders, lozenges, sachets, cachets, elixirs, suspensions, emulsions, solutions, syrups, aerosols, ointments, soft and hard gelatin capsules, suppositories, sterile injectable solutions and sterile packaged powders.

It is still further contemplated that the valienamine-related disaccharide compound can be incorporated as a part of a liposome or a micelle which can then be formulated into a pharmaceutical composition.

The active compound is effective over a wide dosage range and is generally administered in a pharmaceutically effective amount. It will be understood, however, that the amount of the compound actually administered will be determined by a physician, in the light of relevant circumstances, including the condition to be treated, the chosen routes of administration, the actual compound administered, the age, weight and response of the individual patient, the severity of the patient's symptoms and the like.

2-A. Preparation of Valienamine-Related Compounds

The valienamine-related disaccharide compounds are readily prepared by complete chemical syntheses known in the art.

Chemical modifications include the introduction of a chloro, methoxy or amino group or other amino functionalities or the removal of an —OH functionality (i.e. the formation of a deoxy substituent), preferably to the 5-hydroxymethyl position of the valienamine and validamine or the 1-hydroxymethyl position of valiolamine.

Figure 2:
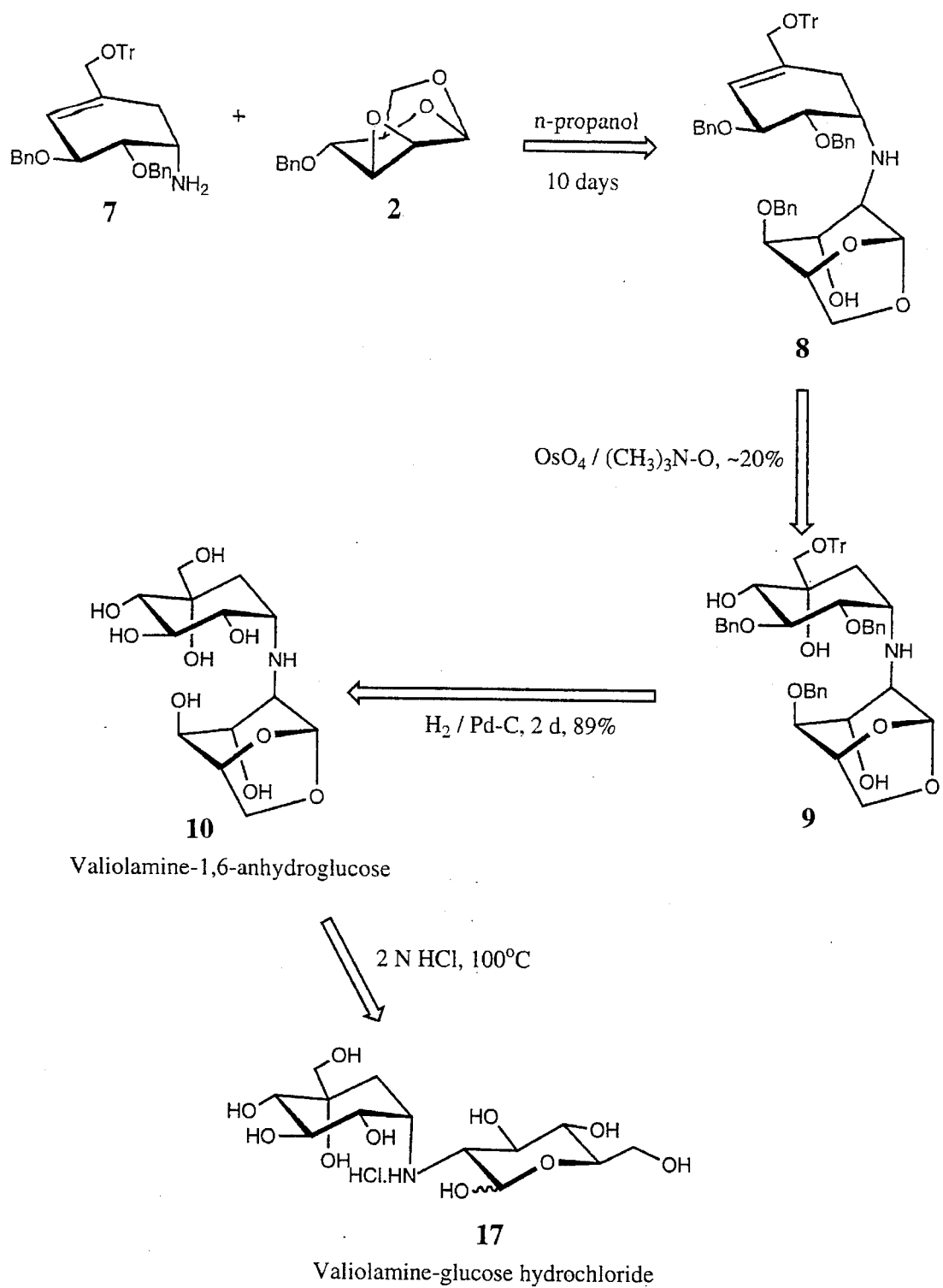
FIG. 2 illustrates the synthesis of valiolamine-1,6-anhydroglucose.
Figure 3:
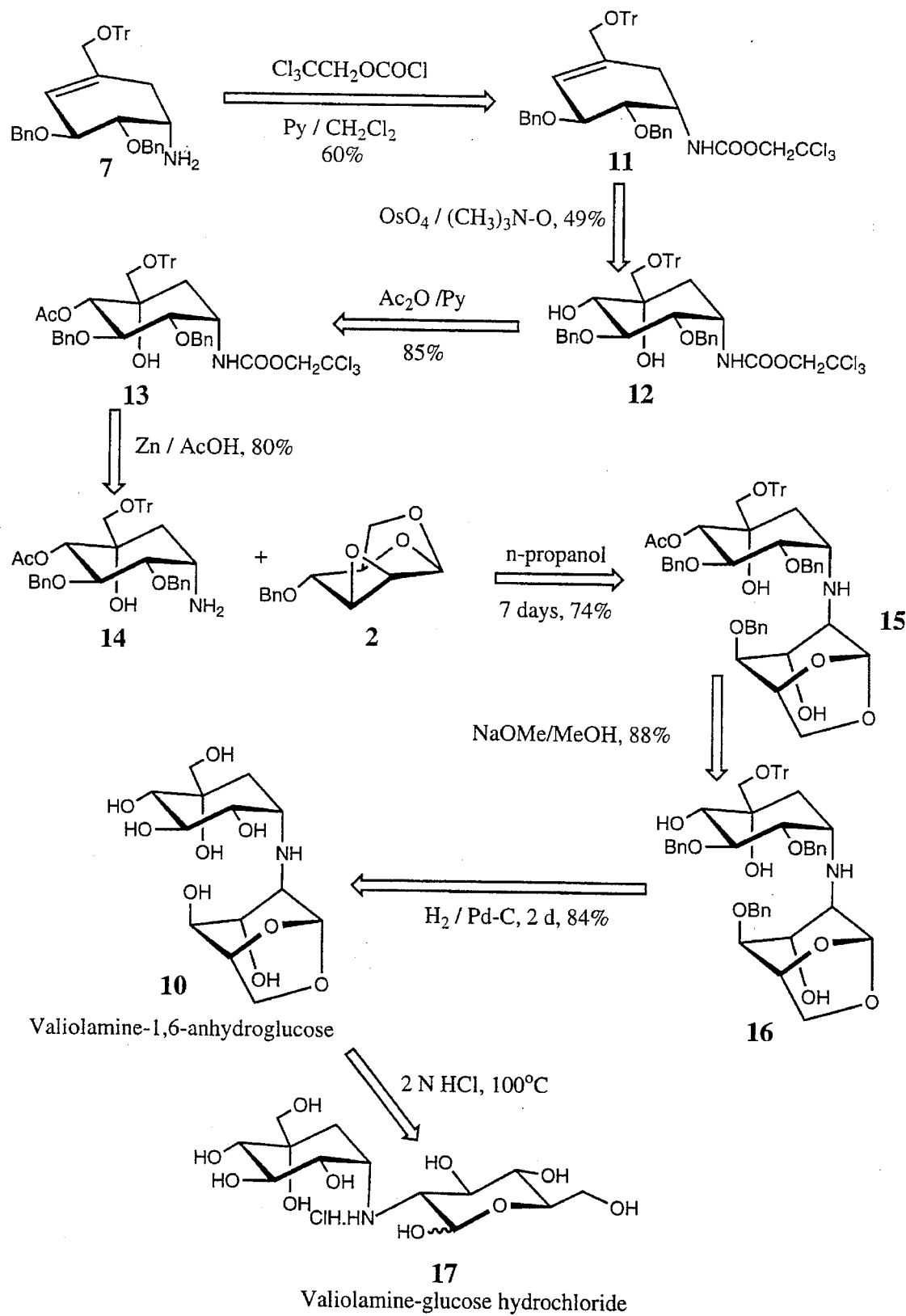
FIG. 3 illustrates an alternate method for the synthesis of valiolamine- 1,6-anhydroglucose.
Figure 4:
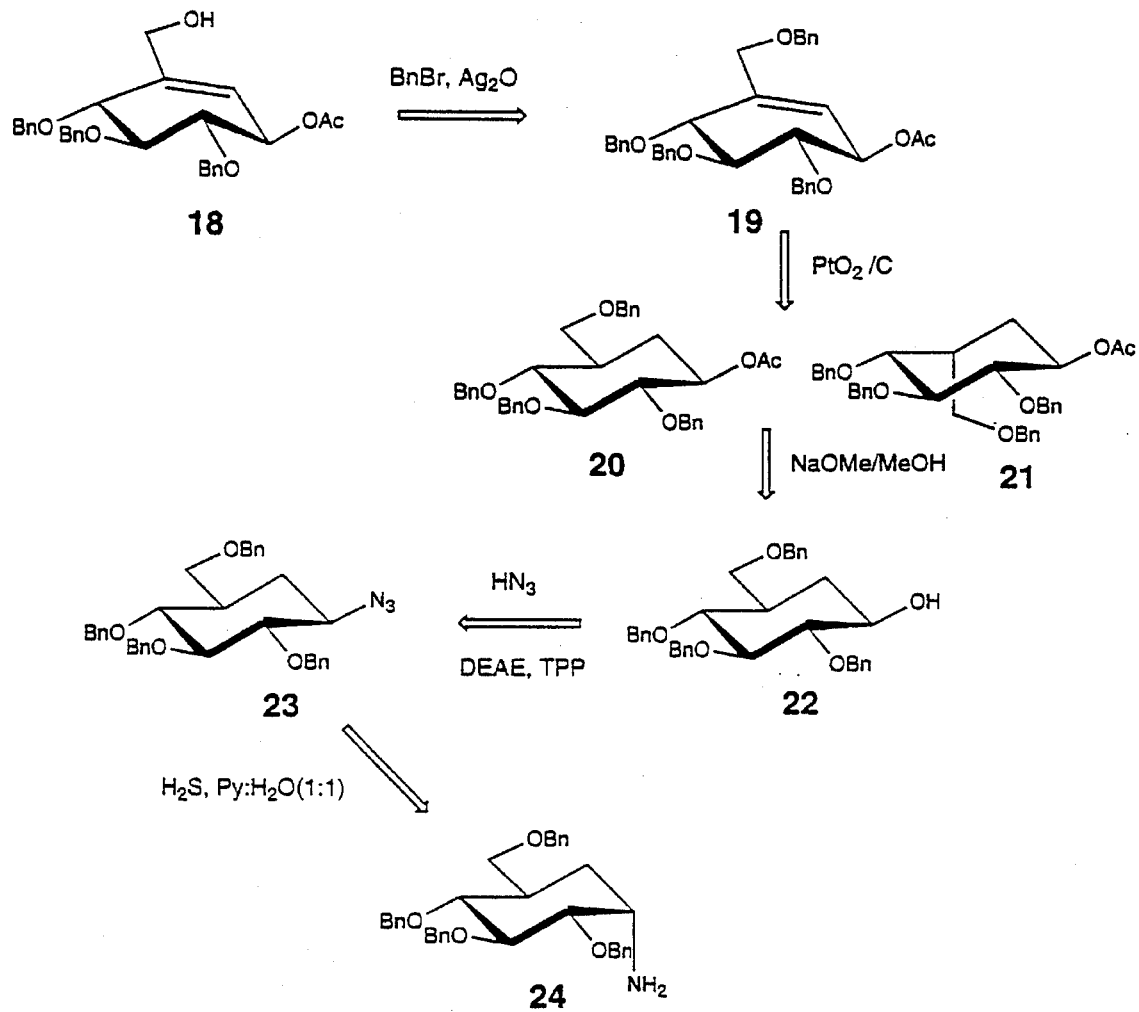
FIG. 4 illustrates the synthesis of protected validamine.

Examples 1–6 hereinbelow and FIGS. 1–4 attached hereto elaborate on the synthetic schemes which result in the preparation of valienamine-related compounds. Well known modifications of these procedures will lead to other such valienamine-related compounds.

2-B. Preparation of valienamine-1,6-anhydroglucose, valienamine-glucose, valiolamine-1,6-anhyclroglucose, valiolamine-glucose, validamine-1,6-anhydroglucose, validamine-glucose and protected validamine FIGS. 1–4 illustrate the synthesis of valienamine-1,6-anhydroglucose, valienamine-glucose, valiolamine-1,6-anhydroglucose and protected validamine.

Specifically the synthesis of valienamine-1,6-anhydroglucose can be carried out in three steps, Coupling of known (1R)-(1,2,4/3)-2,3,4-tribenzyl-5-benzyloxy-methylcyclohex-5-enylamine (compound 1)[3] with the known epoxide, 1,6-anhydro-4-O-benzyl-2,3-epoxy-glucose (compound 2)[4] in N-propanol at 90° C. for four days affords preferentially the desired amine (compound 3). Compound (3) can then be treated with sodium in liquid ammonia in tetrahydrofuran to provide the debenzylated derivative (not shown). This can then be acetylated without any further purification to obtain compound (4). Deacetylation is then carried out using a catalytic amount of sodium methoxide in methanol to provide valienamine-1,6-anhydroglucose (compound 5).

The synthesis of valienamine-glucose hydrochloride can be carried out by the complete deprotection of compound (5). This can be effected by reacting compound (5) with 2N HCl and heating at 100° C. to provide valienamine-glucose hydrochloride (compound 6). Formation of the free base follows conventional methods, e.g., adjustment of pH.

The synthesis of valiolamine-1,6-anhydroglucose can be carried out using two different schemes. In the first methodology, known compound (7)[5] can be coupled with the known epoxide (compound 2) by reacting the compounds in N-propanol for 10 days to provide the 1-6-anhydrodisaccharide (compound 8). Oxidation of compound (8) with osmium tetraoxide in the presence of trimethylamine N-oxide[6] provides for compound (9). Compound (9) can be hydrogenareal with 5% palladium on carbon for simultaneous removal of the benzyl and trityl groups to obtain valiolamine-1,6-anhydroglucose (compound 10)

In the second methodology, compound (7)[5] can be converted into its N-trichloroethylformate derivative (compound 11) by reacting with trichloroethylchloroformate in a mixture of dichloromethane and pyridine. Compound 11 is then oxidized at 60°–70° C. with a catalytic amount of osmium tetraoxide in the presence of trimethylamine-N-oxide[6] giving a valiolamine derivative (compound 12). The resulting compound (12) can be acetylated with acetic anhydride and pyridine to provide compound (13). Removal of the trichloroethylformyl group can then be carried out using zinc in acetic acid to obtain compound (14). Coupling of compound (14) and known epoxide (compound 2)[4] can then be carried out in N-propanol at 90° C. for a week to obtain the protected disaccharide (compound 15). Saponification of compound 15 with sodium methoxide in methanol will provide the disaccharide, compound (16). Compound (16) can be catalytically hydrogenareal with 5% palladium on carbon for simultaneous removal of the benzyl and trityl groups to obtain compound (10).

The synthesis of valiolamine-glucose hydrochloride can be carried out by the complete deprotection of compound (10). This can be effected by reacting compound (10) with 2N HCl and heating at 100° C. to provide valiolamine-glucose hydrochloride (compound 17).

Synthesis of a suitably protected validamine monosaccharide (compound 24) was carried out by readily available starting material (Paulson et al., *Liebigs Ann Chem.* 125–131 1987[10]. The starting material was benzylated by benzyl bromide and silver oxide. Reduction of the double bond by PtO$_2$/C provided compound 20 along with the iodo configuration (compound 21). Compound 20 was saponified by NaOMe in methanol to provide compound 22 which was processed to compound 23 as an azido derivative by reacting compound 22 with hydrazoic acid in the presence of diethylazodicarboxylate (DEAE) and triphenylphosphine (TPP). Hydrogen sulfide reduction of compound 23 in pyridine and water provided 1D-(1,2,4/3,5)-1-amino-2,3,4-tri-O-benzyl- 5-C-benzyloxymethyl-1,2,3,4-cyclohexane tetrol (compound 24) ready for further chain elongation.

The synthesis of validamine-1,6 anhydroglucose and validamine-glucose can be carried out in a manner similar to that described above for valienamine-1,6-anhydroglucose and valienamine-glucose except the starting compound would be 1D-(1,2,4/3,5)-1-amino-2,3,4-tri-O-benzyl-5-C-benzyloxymethyl-1,2,3,4-cyclohexane tetrol (compound 24) rather than (1R)-(1,2,4/3)-2,3,4-tribenxyloxy-5-C1-benzyloxy-methylcyclohex-5-enylamine (compound 1)[3].

As can be appreciated from the disclosure above, the present invention has a wide variety of applications. Accordingly, the following examples are offered by way of illustration and not by way of limitation.

EXAMPLES

In the examples below and figures, the following abbreviations have the following meanings. If not defined below, then the abbreviations have their art recognized meanings.

|   |   |
|---|---|
| Ac | = acetyl |
| Bn | = benzyl |
| DTH | = delayed type hypersensitivity |
| THF | = tetrahydrofuran |
| TR | = trityl |
| g | = gram |
| kg | = kilogram |
| µg | = microgram |
| mmol | = millimolar |
| l | = liter |
| ml | = milliliter |
| µl | = microliter |

Examples A–C illustrate the suppression of antigen-induced inflammation in a mammal by administration of a valienamine-related compounds.

Example A—Inhibition of DTH Inflammatory Response

DTH inflammatory responses were measured using the mouse footpad swelling assay as described by Smith and Ziola[2]. Briefly, groups of Balb/c mice (about 19–20 grams each) were immunized with 100 µg of the OVA antigen (Albumin, Chicken Egg, Sigma, St. Louis, Mo.) containing 20 µg of the adjuvant (DDA—dimethyldioctadecyl-ammonium bromide, Eastman Kodak, Rochester, N.Y.) which also induces a strong inflammatory DTH response in PBS (phosphate buffer saline).

Seven days later, each group of mice was footpad-challenged with 20 µg of the OVA antigen (without adjuvant).

To assess the effect of valienamine-glucose on the inflammatory DTH response, mice received 100 µg of valienamine-glucose five hours after challenge. Control groups were left untreated or received 100 µl of phosphate-buffered saline (PBS). Any resulting inflammatory footpad swelling was measured with a Mitutoyo Engineering micrometer 24 hours after challenge. The amount of footpad swelling observed with treatment with valienamine-glucose was approximately 52% that observed with the control evidencing a significant reduction in inflammation as compared to control.

The above results demonstrate that valienamine-glucose is effective in reducing antigen induced inflammation in a sensitized mammal.

Example B—Inhibition of DTH Inflammatory Response with Valienamine-Related Compounds To assess the effect of valienamine-related compounds on the inflammatory DTH response, groups of Balb/c mice (about 19–20 grams each) were immunized with 100 µg of the OVA antigen containing 20 µg of the adjuvant DDA in PBS.

Seven days later, each group of mice was footpad-challenged with 20 µg of the OVA antigen (without adjuvant).

Five hours after challenge 100 µg of the following compounds were injected as a solution into the tail vein of groups of mice.

1. valienamine-glucose
3. valiolamine-1,6-anhydroglucose
4. valiolamine-glucose

Control groups were left untreated or received 100 µl of phosphate-buffered saline (PBS). Any resulting inflammatory footpad swelling was measured with a Mitutoyo Engineering micrometer 24 hours after challenge. The results are shown in Table I.

TABLE I

| Compound | Amount of Swelling |
|---|---|
| valienamine-glucose | 0.24 mm +/– 0.04 mm |
| valiolamine-glucose | 0.14 mm +/– 0.03 mm |
| valiolamine-1,6-anhydroglucose | 0.28 mm +/– 0.06 mm |
| OVA/PBS | 0.35 mm +/– 0.07 mm |

Mice injected with valiolamine-glucose showed the greatest reduction in the footpad swelling compared to control mice. Mice injected with valiolamine-1,6-anhydroglucose and valienamine-glucose also exhibited reductions in swelling compared to the footpad swelling of control mice.

Example C—Long Term Inhibition of DTH Inflammatory Response

Long term effects of valienamine compounds on the immune response to the OVA antigen were measured a number of weeks after primary immunization (one week after challenge) by measuring the footpad swelling of the mice which received the valienamine compounds as compared to the footpad swelling of control mice.

Forty days after the mice from Example A were footpad-challenged with the OVA antigen, the mice were again footpad-challenged with 20 µg of the OVA antigen (without adjuvant) in the absence of valienamine compounds. The resulting inflammatory footpad swelling was measured with a Mitutoyo Engineering micrometer 24 hours after challenge. The amount of footpad swelling observed with treatment with valienamine-glucose was approximately 60% of that observed with the control.

Fourteen days after the mice from Example B were footpad-challenged each group of mice was again footpad-challenged with 20 µg of the OVA antigen (without adjuvant) in the absence of the valienamine compounds. The resulting inflammatory footpad swelling was measured with a Mitutoyo Engineering micrometer 24 hours after the second challenge. The results are shown in Table II. Again the greatest reduction in foot-pad inflammation was observed with valiolamine-glucose.

TABLE II

| Compound | Amount of Swelling |
| --- | --- |
| valienamine-glucose | 0.28 mm +/– 0.02 mm |
| valiolamine-glucose | 0.17 mm +/– 0.07 mm |
| valiolamine-1,6-anhydroglucose | 0.28 mm +/– 0.05 mm |
| OVA/PBS | 0.37 mm +/– 0.06 mm |

The above results demonstrate that valienamine-related compounds are effective in inducing tolerance to the antigen, thereby resulting in reduced inflammation.

By following the procedures set forth in the above examples, other valienamine-related compounds could be tested to determine whether they could be used to suppress a cell-mediated immune response to an antigen by mere substitution for the valienamine-related compounds described in these examples.

SYNTHESIS

Examples 1–6 below illustrate the synthesis of numerous valienamine-related disaccharide compounds.

Example 1—Synthesis of Valienamine-1,6-anhydroglucose [1,6-anhydro-2-deoxy-2-[1D-(1N,2,4/3)-5-C-hydroxymethyl-2,3,4-trihydroxy-5-cyclohexen-1-yl)amino]-β-D-glucopyranose](Compound 5)

Step A) Synthesis of 1,6-anhydro-4-O-benzyl-2-deoxy-2-[1 D-(1N,2,4/3)-(2,3,4-tri-O-benzyl-5-C-benzyloxymethyl-2,3,4-trihydroxy-5 -cyclohexen-1-yl)amino]-β-D-glucopyranose (Compound 3)

A solution of protected valienamine, (1R)-(1,2,4/3)-2,3,4-tribenzyl-5 -benzyloxy-methylcyclohex-5-enylamine, (Compound 1) made according to the method of Ogawa et al. *J. Chem. Soc. Perkin Trans* (1988)[3] (1.41 g, 2.63 mmol). This was combined with the protected epoxide, 1,6-anhydro-4-O-benzyl-2,3 -epoxy-glucose, made according to the method set forth in Cerny et al., *J. Czechoslav. Chem. Commun* 39 (1974)[4] (compound 2) (3.28 g, 14.0 mmol), in n-propanol (28 ml) and was heated at 90° C. for 4 days. Solvent was evaporated, then co-evaporated with toluene and the residue was chromatographed on a silica gel column using hexane:ethylacetate (2:1) as eluent to provide 1,6-anhydro-4-O-benzyl-2-deoxy-2-[1D-(1N,2,4/3)-(2,3,4 -tri-O-benzyl-5-C-benzyloxymethyl-2,3,4-trihydroxy-5-cyclohexen-1-yl)amino]-β-D-glucopyranose (compound 3) (1.2 g, 59.2%).

Step B) Synthesis of 1,6-anhydro-3-4-di-O-acetyl-2-deoxy-2-[1-D(1N,2,4/3)-(2,3,4-tri-O-acetyl-5-C-acetoxymethyl-2,3,4-trihydroxy-5-cyclohexen-1-yl)amino]-β-D-glucopyranose (Compound 4)

1.09 g (1.41 mmol)of 1,6-anhydro-4-O-benzyl-2-deoxy-2-[1 D-(1N,2,4/3)-2,3,4-tri-O-benzyl-5-C-benzyloxymethyl-2,3,4-trihydroxy-5 -cyclohexen-1-yl)amino]-β-D-glucopyranose (compound 3) was dissolved in THF (20 ml) and liquid ammonia (~100 ml) was added at −78° C. Sodium (0.42 g) was added and the reaction mixture was stirred for 30 minutes at this temperature. $NH_4Cl$(2 g) was then added and ammonia and THF were evaporated at room temperature. The residue was acetylated in pyridine (5 ml) and acetic anhydride (5 ml). Excess of acetic anhydride was quenched by the addition of methanol. The reaction mixture was evaporated and dissolved in dichloromethane (100 ml) and washed sequentially with 5% HCl solution (2×100 ml), saturated $NaHCO_3$ solution (2×100 ml) and water (2×100 ml) before evaporation to a syrup. The syrup was purified by chromatography on silica gel using toluene:ethylacetate (3:1) as eluent to provide 1,6-anhydro-3-4 -di-O-acetyl-2-deoxy-2-[1D-(1N,2,4/3)-(2,3,4-tri-O-acetyl-5 -C-acetoxymethyl-2,3,4-trihydroxy-5-cyclohexen-1-yl)amino]-β-D-glucopyranose (compound 4) (613 mg, 75.8%).

Step C) Synthesis of Valienamine-1,6-anhydroglucose [1,6-anhydro-2 -deoxy-2-[1D-(1N,2,4/3)-5-C-hydroxymethyl-2,3,4-trihydroxy-5 -cyclohexen-1-yl)amino]-β-D-glucopyranose](Compound 5)

482 mg (0.843 mmol)of 1,6-anhydro-3,4-di-O-acetyl-2-deoxy-2 -[1D(1N,2,4/3)-(2,3,4-tri-O-acetyl-5-C-acetoxymethyl-2,3,4-trihydroxy-5 -cyclohexen-1-yl)amino]-β-D-glucopyranose (compound 4) was dissolved in dry methanol (20 ml) and a methanolic solution of sodium methoxide (0.5N, 0.1 ml) was added. After 4 hours, solvent was evaporated and the residue was purified by passing through a column of sephadex using water:ethanol (1:1) as eluent to provide pure 1,6-anhydro-2-deoxy-2-[1D-(1N,2,4/3)-5 -C-hydroxymethyl-2,3,4-trihydroxy-5-cyclohexen-1-yl)amino]-β-D-glucopyranose (compound 5) (249 mg, 92.5%) as white powder after lyophilization.

Example 2—Synthesis of Valienamine-glucose [2-deoxy-2-[1D-(1N, 2,4/3)-(5-C-hydroxymethyl-2,3,4-trihydroxy-5-cyclohexen-1-yl)amino]-D-glucopyranose hydrochloride](Compound 6)

1,6-anhydro-2-deoxy-2-[1D-(1N,2,4/3)-5-C-hydroxymethyl-2,3,4-trihydroxy-5-cyclohexen-1-yl)amino]-β-D-glucopyranose (compound 5) (152.5 mg, 0.47 mmol) was heated at 100° C. in 2N HCl solution for 4 days. Solvent was removed by co-evaporation with water and the residue was purified by chromatography on an Iatrobeads column (Iatron Laboratories, Japan) using chloroform:methanol:water, (65:38:3) as eluent to provide 2-deoxy-2 -[ID-(1N,2,4/3)-(5-C-hydroxymethyl-2,3,4-trihydroxy-5-cyclobexen-1-yl)amino]-D-glucopyranose hydrochloride (compound 6) after lyophilization (116 mg, 65%).

Example 3—Synthesis of Valiolamine-1,6-anhydroglucose [1,6-anhydro-2 -deoxy-2[1D-(1,2,4,5/3)-(1-C-hydroxymethyl-1,2,3,4-tetra-hydroxy-cyclohexyl)amino]-β-D-glucopyranose (Compound 10)

Step A) Synthesis of 1,6-anhydro-4-O-benzyl-2-deoxy-2 [1D-(1/2,3)-1,2 di-O-benzyl-(5-C-trityloxymethyl-1,2-dihydroxy-6-cyclohexenyl)amino]-glucopyranose (Compound 8)

A solution of protected valienamine made according to the procedure set forth in Hayashida et al., *J. Carbohydrate Chemistry* 7(1):83–94 (1988)[5] (compound 7) (150 mg, 0.26 mmol) and epoxide[4] (compound 2) (309.2 mg, 1.32 mmol) in N-propanol (5 ml) was heated at 90° C. for 10 days. Solvent was evaporated, then coevaporated with toluene and the residue was chromatographed on a silica gel column using hexane:ethyl acetate (2:1) as eluent to provide 1,6-anhydro-4-O-benzyl-2-deoxy-2[1D-(1/2,3)-1,2-di-O-benzyl-(5-C-trityloxymethyl-1,2-dihydroxy-6-cyclohexenyl)-amino]-glucopyranose (compound 8) (150 mg, 69.9%).

Step B) Synthesis of 1,6-anhydro-4-O-benzyl-2-deoxy-2 [1D-(1,2,4,5/3)-3,4-di-O-benzyl-(1-C-trityloxymethyl-1,2,3,4 -tetrahydroxy-cyclohexyl)-amino]-β-D-glucopyranose (compound 9)

Osmium tetroxide (2.0 mg) was added to a solution of compound 8 (120 mg, 0.15 mmol) and trimethylamine-N-oxide[6] (32.7 mg, 0.29 mmol) in t-butanol (5 ml) containing pyridine (0.25 ml); the mixture was stirred in argon atmosphere for 6 hours at 60°–70° C., treated with a 20% aqueous solution of sodium hydrogen sulfite (1.0 ml) at room temperature, diluted with saturated brine (10.0 ml) and extracted with dichloromethane (3×20 ml). The extract was washed with water, dried and concentrated. The residue was purified by chromatography on silica gel hexane:ethyl acetate (3:1) as eluent to give 1,6-anhydro-4-O-benzyl-2-deoxy-2[1D-(1, 2,4,5/3)-3,4-di-O-benzyl-(1-C-trityloxymethyl-1,2,3,4-tetrahydroxy-cyclohexyl)-amino]-β-D-glucopyranose (compound 9) (26 mg, 20.8%).

Step C) Synthesis of 1,6-anhydro-2-deoxy-2-[1D-(1,2,4,5/3)-(1 -C-hydroxymethyl-1,2,3,4-tetrahydroxy-cyclohexyl) amino]-β-D-glucopyranose (Compound 10)

Compound 9 (20 mg, 0.024 mmol) was dissolved in methanol (5 ml) containing 0.1% hydrochloric acid. Pd(OH)$_2$ on carbon (50 mg) was added and the reaction mixture stirred at atmospheric pressure for 2 days to give 1,6 -anhydro-2-deoxy-2-[1D-(1,2,4,5/3)-(1-C-hydroxymethyl-1,2,3,4-tetrahydroxycyclohexyl)amino]-β-D-glucopyranose (compound 10) (7 mg, 89%).

Example 4—Alternate synthesis of Valiolamine-1,6-anhydroglucose [1,6 anhydro-2-deoxy-2-[1D-(1,2,4,5/3)-(5-C-hydroxymethyl-1,2,3,4-tetrahydroxy-cyclohexyl)-amino]-β-D-glucopyranose (Compound 10)

Step A) Synthesis of 1D-(1/2,3)-1,2-di-O-benzyl-3-(trichloroethylamino)5 -(trityloxymethyl)-6-cyclohexene-1,2-diol (compound 11).

A solution of trichloroethylchloroformate (308 mg, 1.45 mmol) in dichloromethane (2 ml) was added dropwise at 0° C. to a solution of protected valienamine (compound 7) made according to the method of Hayashida et al., *J. Carbohydrate Chemistry* 7(1):83–94 (1988)[5] (550 mg, 0.97 mmol) in pyridine (4 ml) and dichloromethane (5 ml). The mixture was stirred overnight at room temperature, diluted with water (20 ml), stirred for a further 2 hours and extracted with dichloromethane (20 ml×3). The extract was washed with 1M hydrochloric acid, aqueous sodium hydrogencarbonate, and sodium chloride, dried and concentrated. The residue was chromatographed on silica gel using benzene:ethyl acetate (98:2) as eluent to provide 1D-(1/2,3)-1,2-di-O-benzyl-3 -(trichloroethylamino)-5-(trityloxymethyl)-6-cyclohexene-1,2-diol (compound 11) (430 mg, 59.7%).

Step B) Synthesis of IL-(1,2,4,5/3)-3,4-di-O-benzyl-5 (trichloroethylamino)-1-C-(trityloxymethyl)-cyclohexane-1,2,3,4 -tetrol (Compound 12).

Osmium tetroxide (3.0 mg, 0.01 mmol) was added to a solution of compound (11) (350 mg, 0.47 mmol) and trimethylamine-N-oxide made according to the method of Ray and Matteson *Tetrahedron Lett.* 21:449 (1980)[6] (104.7 mg, 0.94 mmol) in t-butanol (10 ml) containing pyridine (0.5 ml). The mixture was stirred in argon atmosphere for 6 hours at 60°–70° C., treated with 20% aqueous solution of sodium hydrogen sulfite (2 ml) at room temperature, diluted with saturated brine (20 ml) and extracted with dichloromethane (3×20 ml). The extract was washed with water, dried and concentrated. The residue was purified by chromatography on silica gel using benzene:ethyl acetate (96:4) as eluent to give a syrup of IL-(1,2,4,5/3)-3,4-di-O-benzyl-5 -(trichloroethylamino)-1-C-(trityloxymethyl)-cyclohexane-1,2,3,4- tetrol (compound 12) (182 mg, 48.8%). Apparently, cis-dihydroxylation of the c—c double bond took place exclusively from the α-side, as no compound, which should have been produced by the attack from the opposite side was detected.

Step C) Synthesis of IL-(1,2,4,5/3)-2-O-acetyl-3,4-di-O-benzyl-5 -(trichloroethylamino)-1-C-(trityloxymethyl)-cyclohexane-1,2,3,4 -tetrol (Compound 13).

Acetic anhydride (2 ml) was added at 0° C. to a solution of compound (12) (160 mg, 0.20 mmol) in dichloromethane (5 ml) and pyridine (2 ml); the mixture was stirred overnight at room temperature diluted with water (10 ml), stirred for a further 2 hours and extracted with dichloromethane (3×20 ml). The extract was successfully washed with 1M hydrochloric acid and brine and concentrated. The residue was purified by chromatography on silica gel using benzene:ethyl acetate (9:1) as eluent to provide IL-(1,2,4,5/3)-2-O-acetyl-3,4 -di-O-benzyl-5-(trichloroethylamino)-1-C-(trityloxymethyl)-cyclohexane-1,2,3,4-tetrol (compound 13) (145 mg, 86%).

Step D) Synthesis of 1L-(1,2,4,5/3)-2-O-acetyl-3,4-di-O-benzyl-5 -amino-1-C-(trityloxy-methyl)-cyclohexane-1, 2,3,4-tetrol (Compound 14)

Compound (13) (140 mg, 0.17 mmol) was treated with fresh zinc in 80% aqueous acid for 5–10 hours at room temperature until all the starting material was converted into product. The product was filtered, evaporated and the residue was purified by chromatography on silica gel using benzene:ethyl acetate (9:1) as eluent to provide 1L-(1,2,4, 5/3)-2-O-acetyl-3,4-di-O-benzyl-5 -amino-1-C-(trityloxymethyl)-cyclohexane-1,2,3,4-tetrol (compound 14) (88 mg, 80%).

Step E) Synthesis of 1,6-anhydro-4-O-benzyl-2-deoxy-2-[1 D-(1,2,4,5/3)-2-O-acetyl-3,4-di-O-benzyl-(1-C-trityloxymethyl-1,2,3,4-tetrahydroxy-cyclohexyl)-amino]-glucopyranose (Compound 15).

A solution of compound 14 (80 mg, 0.12 mmol) and epoxide (compound 2) (146 mg, 0.61 mmol) in N-propanol (3 ml) was heated at 90° C. for 7 days. Solvent was evaporated, co-evaporated with toluene and the residue was chromatographed on a silica gel column using hexane:ethyl acetate (2:1) as eluent to provide 1,6-anhydro-4-O-benzyl-2-deoxy-2-[1D-(1,2,4,5/3)-2 -O-acetyl-3,4-di-O-benzyl-(1-C-trityloxymethyl-1,2,3,4-tetrahydroxy-cyclohexyl)-amino] glucopyranose (compound 15) (80 mg, 74%).

Step F) Synthesis of 1,6-anhydro-4-O-benzyl-2-[1D-(1,2,4, 5/3)-3,4 -di-O-benzyl-(1-C-trityloxymethyl-1,2,3,4-tetrahydroxy-cyclohexyl)-amino]-glucopyranose (Compound 16).

Compound (15) (75 mg, 0.084 mmol) was deacetylated by sodium methoxide in methanol (0.5M solution) by stirring the reaction mixture for 3 hours at room temperature to give 1,6-anhydro-4-O-benzyl-2-[1 D-(1,2,4,5/3)-3,4-di-O-benzyl-(1-C-trityloxymethyl-1,2,3,4-tetrahydroxy-cyclohexyl)-amino]glucopyranose (compound 16) (63 mg, 88%).

Step G) Synthesis of 1,6-anhydro-2-deoxy-2-[1D-(1,2,4,5/3)-(1 -C-hydroxymethyl-1,2,3,4-tetrahydroxy-cyclohexyl)-amino]-β-D-glucopyranose (Compound 10).

Compound (16) (50 mg, 0.06 mmol) was dissolved in methanol (5 ml) containing 0.1% hydrochloric acid. Pd(OH)$_2$ on carbon (50 mg) was added and the reaction mixture stirred at atmospheric pressure for 2 days to give 1,6 -anhydro-2-deoxy-2-[1D-(1,2,4,5/3)-(1-C-hydroxymethyl-1,2,3,4 -tetrahydroxy-cyclohexyl)-amino]-β-D-glucopyranose (compound 10) (16.5 mg, 83.7%).

Example 5—Synthesis of Valiolamine-glucose (Compound 17)

1,6-anhydro-2-deoxy-2-[1D-(1,2,4,5/3)-(1-C-hydroxymethyl-1,2,3,4 -tetrahydroxy-cyclohexyl)-amino]-β-D-glucopyranose (compound 10) (20 mg, 0.059%) was heated at 100° C. in 2N HCl solution for 4 days. Solvent was removed by co-evaporation with water and the residue was purified by chromatography on an latrobeads column (Iatron Laboratories, Japan) using chloroform:methanol:water, (65:38:3) as eluent to provide valiolamine- glucose-hydrochloride (compound 17) after lyophilization (15 mg, 71.2%).

Example 6—Synthesis of Protected Validamine for the preparation of Validamine- 1,6-anhydroglucose and validamine-glucose hydrochloride Step A) Synthesis of 1L(1,3/2,4)-1-O-Acetyl-2,3,4-tri-O-benzyl-5 -C-benzyloxymethyl-5-cyclohexene-1,2,3,4-tetrol (Compound 19)

1.21 g (2.47 mmol) of compound 18 (Paulson et al., *Liebigs Ann. Chem.* 125–131 (1987))[10] was dissolved in pyridine (3.0 ml). Benzyl bromide (0.60 ml) was added followed by silver oxide (0.96 g). After 20 hours and 48 hours, more silver oxide was added in 0.48 g and 0.8 g quantities respectively. After 3 days, methanol was added and the mixture was stirred for 1 hour. The organic salts were filtered off. The filtrate was diluted with dichloromethane and washed with saturated sodium hydrogencarbonate solution and water, dried over $Na_2SO_4$ and evaporated. The syrup was purified by chromatography on silica gel using hexane:ethyl acetate (6:1) as eluent. Pure compound 19 (852 mg, 84% based on consumption of the starting material) was obtained along with recovered starting material (347 mg).

Step B) Synthesis of 1L-(1,3,5/2,4)1-O-acetyl-5 -C-benzyloxymethyl-2,3,4-tri-O-benzyl-1,2,3,4-cyclohexane tetrol (20) and Pseudo-L-iodopyranose isomer (21).

Compound 19 (137.6 mg, 0.24 mmol) was dissolved in ethanol (4.0 ml) and $PtO_2$ catalyst was added (4 mg). The reaction mixture was stirred for 1 hour at room temperature and atmospheric pressure until most of the starting material was consumed. Chromatography of the material, after filtration of the catalyst on the pad of celite and evaporation, provided compound 20 (70 mg, 50.6%) and its α-iodo isomer compound 21 (60 mg, 43.5%). Chromatography was carried out twice: first using ethyl acetate:hexane (9:1) as eluent and the second time using carbon tetrachloride:hexane (4:1) as eluent.

Step C) Synthesis of 1L-(1,3,5/2,4)-5-C-benzyloxymethyl-2,3,4 -tri-O-benzyl-1,2,3,4-cyclohexane tetrol (Compound 22)

Compound 20 (79 mg, 0.12 mmol) was dissolved in 5 ml of methanol and a catalytic amount of sodium methoxide in methanol (0.5 ml, 0.5N) was added to it. After stirring the reaction mixture for 1 hour at room temperature, it was neutralized by 1R-120-H$^+$ (Amberlite) resin. The resulting compound was filtered from the resin and evaporated to dryness to obtain compound 22 (55 mg, 85%).

Step D) Synthesis of 1D-(1,2,4/3,5)-1-azido-2,3,4-tri-O-benzyl-5 -C-benzyloxymethyl-1,2,3,4-cyclohexane tetrol (Compound 23)

A benzene solution of hydrazoic acid (10%, 3.0 mL) was added to a mixture of compound 22 (50 mg, 0.093 mmol) and triphenylphosphine (TPP) (97.4 mg, 0.37 mmol) in toluene (3.0 ml) and the whole mixture was thoroughly cooled. Diethylazodicarboxylate (DEAE) (0.1 ml) was added dropwise to the mixture, with stirring, at a temperature below −10° and kept there for 30 minutes and for an additional 2 hours at room temperature. The precipitate was filtered off, and the filtrate was evaporated. The residue was chromatographed with benzene as the eluent, to provide a syrup (compound 23) (42 mg, 80.3%).

Step E) Synthesis of 1D-(1,2,4/3,5)-1-amino-2,3,4-tri-O-benzyl-5 -C-benzyloxymethyl-1,2,3,4-cyclohexane tetrol (Compound 24)

Hydrogen sulfide was bubbled through a solution of compound 23 (40 mg, 0.071 mmol) in a mixture of pyridine (1 ml) and water (1.0 ml) for 2 hours at room temperature. The excess of $H_2O$ was removed by a stream of nitrogen. The reaction mixture was concentrated and the residue was purified on silica gel using benzene:ethyl acetate (9:1) as eluent to provide pure compound 24 (35 mg, 91.7%).

Compound 24 can be used in a method of synthesis similar to that provided above for the synthesis of valienamine-1,6-anhydroglucose and valienamine-glucose hydrochloride to synthesize validamine-1,6-anhydroglucose and validamine-glucose hydrochloride.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

What is claimed is:

1. A method for reducing the degree of inflammation in a mammal arising from the initiation of a mammal's secondary immune response due to antigen exposure, which method comprises administering to said mammal an valienamine-related disaccharide compound selected from the group consisting of Formula I

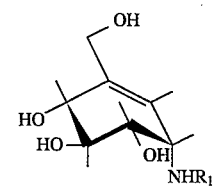

and Formula II

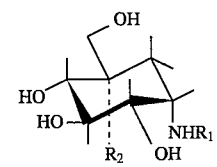

where $R_1$ is selected from the group consisting of glucose and 1,6-anhydroglucose;

where $R_2$ is selected from the group consisting of —H and —OH; and pharmaceutically acceptable salts thereof.

2. The method of claim 1 wherein the amount of valienamine-related disaccharide compound administered to said mammal comprises from 5 mg to about 20 mg/kg.

3. The method of claim 1 wherein the amount of valienamine-related disaccharide compound administered to said mammal comprises from 5 mg to about 20 mg/kg.

4. The method of claim 1 wherein the inflammation arising from the initiation of a mammal's secondary immune response due to antigen exposure is inflammation due to psoriasis, asthma, dermatitis, rheumatoid arthritis, delayed type hypersensitivity, inflammatory bowel disease, multiple sclerosis, viral pneumonia or bacterial pneumonia.

5. The method of claim 1 wherein said valienamine-related disaccharide compound is administered at least 0.5 hours after initiation of said mammal's immune response.

6. A method for reducing the degree of inflammation in a mammal arising from the initiation of a mammal's secondary immune response due to antigen exposure, which method comprises administering to said mammal an valienamine-related disaccharide compound selected from the group consisting of valienamine-glucose, valiolamine-1,6- anhydroglucose and valiolamine-glucose and pharmaceutically acceptable salts thereof.

7. The method of claim 6 wherein said valienamine-related disaccharide compound is valienamine-glucose.

8. An α-5,2-valiolamine disaccharide of the structure

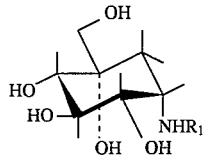

where $R_1$ is selected from the group consisting of glucose and 1,6-anhydroglucose; and pharmaceutically acceptable salts thereof.

9. An α-1,2-valienamine-related disaccharide selected from the group consisting of Formula I

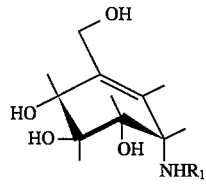   I and Formula II

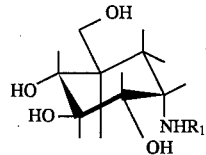   II where $R_1$ is selected from the group consisting of glucose and 1,6-anhydroglucose; and pharmaceutically acceptable salts thereof.

10. A pharmaceutical composition comprising a pharmaceutically inert carrier and an α-5,2-valiolamine disaccharide of

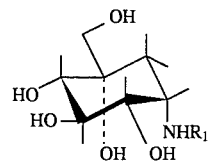

where $R_1$ is selected from the group consisting of glucose and 1,6-anhydroglucose; and pharmaceutically acceptable salts thereof.

11. A pharmaceutical composition comprising a pharmaceutically inert carrier and an α1,2-valienamine-related disaccharide selected from the group consisting of Formula I

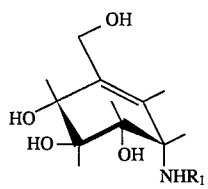   I and Formula II

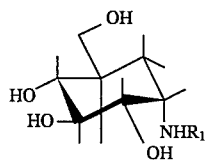   II where $R_1$ is selected from the group consisting of glucose and 1,6-anhydroglucose; and pharmaceutically acceptable salts thereof.

* * * * *